(12) United States Patent
Boustta et al.

(10) Patent No.: US 9,687,552 B2
(45) Date of Patent: Jun. 27, 2017

(54) ASSOCIATION OF POLY(N-ACRYLOYLGLYCINAMIDE) WITH AT LEAST ONE ACTIVE PRINCIPLE

(71) Applicants: CENTRE NATIONAL DE LA RECHERCHE SCIENTIFIQUE, Paris (FR); INSTITUT REGIONAL DU CANCER DE MONTPELLIER, Montpellier (FR); UNIVERSITE DE MONTPELLIER 1, Montpellier (FR)

(72) Inventors: Mahfoud Boustta, Pignan (FR); Pierre-Emmanuel Colombo, Montpellier (FR); Michel Vert, Castelnau-le-Lez (FR)

(73) Assignees: CENTRE NATIONAL DE LA RECHERCHE SCIENTIFIQUE, Paris (FR); INSTITUT REGIONAL DU CANCER DE MONTPELLIER, Montpellier (FR); UNIVERSITE DE MONTPELLIER 1, Montpellier (FR)

( * ) Notice: Subject to any disclaimer, the term of this patent is extended or adjusted under 35 U.S.C. 154(b) by 108 days.

(21) Appl. No.: 14/381,462

(22) PCT Filed: Feb. 26, 2013

(86) PCT No.: PCT/IB2013/051536
§ 371 (c)(1),
(2) Date: Aug. 27, 2014

(87) PCT Pub. No.: WO2013/128373
PCT Pub. Date: Sep. 6, 2013

(65) Prior Publication Data
US 2015/0122695 A1 May 7, 2015

(30) Foreign Application Priority Data
Feb. 27, 2012 (FR) ..................... 12 51765

(51) Int. Cl.
| A61K 9/00 | (2006.01) |
| A61K 49/04 | (2006.01) |
| A61K 47/32 | (2006.01) |
| A61K 9/10 | (2006.01) |
| A61J 1/20 | (2006.01) |
| A61K 9/06 | (2006.01) |

(52) U.S. Cl.
CPC ............. *A61K 47/32* (2013.01); *A61J 1/2093* (2013.01); *A61K 9/0024* (2013.01); *A61K 9/06* (2013.01); *A61K 9/10* (2013.01); *A61K 49/04* (2013.01); *A61K 49/0404* (2013.01); *A61K 49/0409* (2013.01)

(58) Field of Classification Search
CPC ................. A61K 9/00; A61K 49/00
See application file for complete search history.

(56) References Cited

U.S. PATENT DOCUMENTS

| 7,976,728 B2 * | 7/2011 | Eguchi | C08F 220/58 252/380 |
| 2009/0053276 A1 * | 2/2009 | Richard | A61K 9/0019 424/422 |

FOREIGN PATENT DOCUMENTS

| EP | 1 312 627 A1 | 5/2003 |
| JP | A-2008-220868 | 9/2008 |

OTHER PUBLICATIONS

I.M. El-Sherbiny et al., Preparation, Characterization, swelling and in vitro drgu release behaviour of poly[N-acryloylglycine-chitosan] interpolymeric pH and thermally-responsive hydrogels, European Polymer Journal, 41, 2584-2591, 2005.*
Kuilin Deng et al. A pH/Thermo-responsive Injectable Hydrogel System Based on Poly(N-acryloylglycine) as a Drug Carrier, Iranian Polymer Journal. 20(3), 2011, 185-194.*
Jun. 13, 2013 International Search Report issued in International Application No. PCT/IB2013/051536.
Jun. 13, 2013 Written Opinion issued in International Application No. PCT/IB2013/051536.
Haas et al., "Differential Thermal Analysis of Thermally Reversible Gels," *Analytical Calorimetry*, 1970, vol. 2, pp. 211-223.
Haas et al., "Synthetic Thermally Reversible Gel Systems. IV," *Journal of Polymer Science*, 1970, vol. 8, pp. 1213-1226.
Haas et al., Synthetic Thermally Reversible Gel Systems. II, *Journal of Polymer Science*, 1967, vol. 5, Part A-2, pp. 915-927.
Glatzel et al., "Well-defined synthetic polymers with a protein-like gelation behavior in water," *ChemComm*, 2010, vol. 46, pp. 4517-4519.
Hass et al., "Thermally reversible homopolymer gel systems", *Journal of Polymer Science*, Part B, 1964, vol. 2, pp. 1095-1097.
Glatzel et al., "Well-Defined Uncharged Polymers with a Sharp UCST in Water and in Physiological Milieu," *Macromolecules*, 2011, vol. 44, 413-415.
Work et al., "Definitions of Terms Related to Polymer Blends, Composites, and Multiphase Polymeric Materials," *Pure Appl. Chem.*, 2004, vol. 76, No. 11, pp. 1985-2007.
Aguilar et al., "Smart Polymers and Their Applications as Biomaterials," *Topics in Tissue Engineering*, 2007, vol. 3, pp. 1-27.
Deng et al., "A pH/Thermo-responsive Injectable Hydrogel System Based on Poly(N-acryloylglycine) as a Drug Carrier," *Iranian Polymer Journal*, 2011, vol. 20, No. 3, pp. 185-194.

* cited by examiner

*Primary Examiner* — Michael G Hartley
*Assistant Examiner* — Jagadishwar Samala
(74) *Attorney, Agent, or Firm* — Oliff PLC

(57) ABSTRACT

The present invention relates to an association of poly (N-acryloyl glycinamide) with at least one active principle and/or at least one product which is visible in medical imaging, in a physiologically acceptable aqueous medium.

10 Claims, 3 Drawing Sheets

ASSOCIATION OF POLY(N-ACRYLOYLGLYCINAMIDE) WITH AT LEAST ONE ACTIVE PRINCIPLE

The present invention relates to galenical formulations formed from smart polymers, and more particularly from heat-reactive polymers having in aqueous solution an upper critical solution temperature (UCST) compatible with the reversible formation of a gel phase by cooling of a hot solution when they are placed in contact with the human or animal body, in particular during the cooling phase.

The terms "smart polymer", "adaptive polymer" and "reactive polymer" mean a polymer that is capable of responding to an external stimulus by a change of properties. This external stimulus may be, for example, temperature, pressure, pH, ionic strength, light or a mechanical, electrical or magnetic stimulus. Such a type of polymer is also commonly referred to as a stimuli-responsive polymer. Usually, the conformation of the polymer chains is modified in response to the stimulus, imparting the change of properties. This modification of conformation is generally associated with a chemical modification, these two modifications being simultaneous, reversible (association by hydrogen bonding, ionic bonding or dipolar bonding, solvatation or desolvatation) or irreversible (chemical isomerism), and usually of cooperative nature.

It is known practice to use or, more generally, only to propose to use some of these smart polymers in the biomedical field. Reference may be made, for example, to the article "*Smart Polymers and Their Applications as Biomaterials*", Aguilar et al., Topics in Tissue Engineering, 2007, Vol. 3.

Among said smart polymers already used in the field of releasing active principles, pH-sensitive polymers have been described in particular. Temperature-sensitive polymers and more particularly polymers having a lower critical solution temperature (LCST) corresponding to a solution phase at low temperature below the LCST and to a more or less solid condensed phase above it, have also been described.

Systems of UCST type characterized by a more or less solid condensed phase at low temperature below the UCST and a liquid phase above it also exist. In these systems, the condensed phase consists of a water-swollen hydrophilic gel, in contrast with the condensed phases of LCST type which are largely desolvated and have a much less pronounced hydrogel nature (presence of internal water) above the LCST.

Among the systems of LCST type are poly(N-isopropylacrylamide)s, which are known under the abbreviations PNIPAM, PNIPAAm or polyNIPAM, or alternatively copolymers containing blocks of (A-B) diblock or (A-B-A or B-A-B) triblock type in which A is a poly(ethylene oxide) segment and B is a poly(lactic acid) segment, or alternatively diblock or triblock copolymers in which A is a poly(ethylene oxide) segment and B is a poly(propylene oxide) segment. Among the compounds of LCST type, poly(N-isopropylacrylamide) has been particularly studied for biomedical applications.

Poly(N-isopropylacrylamide) has a reversible sol-gel transition temperature at about 32° C. in aqueous solution which is compatible with human and animal organisms. This variable temperature may be modified by copolymerization with comonomers, especially those that introduce hydrophobic or ionic or even hydrophilic species.

Poly(N-acryloylglycinamide), known under the abbreviations PAG and PNAG, is moreover known, and was described for the first time by Haas in the 1960s in a series of publications between 1964 ("*Thermally reversible homopolymer gel systems*", Hass et al., Journal of Polymer Science, Part B, 1964, Vol. 2, 12:1095) and 1970 ("*Differential thermal analysis of thermally reversible gels*", Haas et al., Anal. Calorimetry, Proc. Symp., 1970, 2:211). Furthermore, US 2009/0053276 discloses an injectable composition which contains heat-sensitive hydrogel particles, including particles formed from polymers with a UCST. However, poly(N-acryloylglycinamide)s are not described therein and the only phenomenon sought is the expansion of the particles by heating at the temperature of the human body.

A polymer with a UCST, which is thus injectable as a solution, is also known from Kuilin Deng et al. (Iranian Polymer Journal, 2011, Vol, 20. 3:185). However, poly(N-acryloylglycinamide)s are not described in there either, and the utility of the polymer described for delivering active principles by injection is not adapted to the thermal conditions of the parenteral route.

Some authors have also studied the properties of PAGs obtained via the reversible addition-fragmentation transfer (RAFT) polymerization method. However, the PACGs obtained via this polymerization method do not have a gel-sol transition temperature. The absence of gel-sol transition for the PAGs obtained by RAFT polymerization is moreover underlined in the article "*Well-defined uncharged polymers with a sharp UCST in water and in physiological milieu*", Glatzel S. et al., Macromolecules, 2011, 44:413.

The inventors have demonstrated that the use of poly(N-acryloylglycinamide) having a gel-sol transition temperature in a galenical formulation comprising an active principle for the purpose of topical application in order to release and diffuse said active principle locally, has many advantages, although poly(N-acryloylglycinamide) had never been proposed in this application.

Thus, one subject of the present invention is the combination of poly(N-acryloylglycinamide) with at least one active principle and/or at least one product that is visible in medical imaging, in a physiologically acceptable aqueous medium.

A subject of the invention is also the combination as defined above, in which said poly(N-acryloylglycinamide) has an average molar mass of between 10 000 and 1 000 000 g/mol, in particular between 30 000 and 600 000 g/mol, or even between 40 000 and 200 000 g/mol.

Preferably, the combination according to the invention has a gel-sol transition temperature of between 30 and 60° C. and preferably between 38 and 50° C., measured, for example, via the inverted tube method.

More particularly, the combination according to the invention is in liquid form above the gel-sol transition temperature and in gel form below the gel-sol transition temperature.

More particularly, depending on the site of application under consideration, a combination with a gel-sol transition temperature above the temperature of the site of application is chosen. For example, if the site of application under consideration is the intraperitoneal cavity, a combination with a gel-sol transition temperature above 37° C. will be chosen. Similarly, a combination with a gel-sol transition temperature above 30° C. will be chosen if the site of application under consideration is the skin.

According to another aspect, the present invention also relates to the combination as defined above, which is useful for delivering active principles.

According to yet another aspect, the present invention relates to the use of poly(N-acryloylglycinamide) with an average molar mass of between 10 000 and 1 000 000 g/mol, in particular between 30 000 and 600 000 g/mol, or even between 40 000 and 200 000 g/mol, for the preparation of a gelable aqueous solution comprising an active principle and/or a product that is visible in medical imaging.

With regard to the properties of the combination in gel form in accordance with the present invention, and in particular its good adhesion to tissue, one of the applications more particularly targeted in the context of the present invention concerns the delivery of active principles intended for local peroperative antitumor treatment, especially complementary to a tumor reduction surgery, for example an abdominal cancer in peritoneal carcinomatosis.

Specifically, this particular application meets the need of carcinology surgeons to have available a reliable postoperative treatment. Specifically, when the surgeon has just performed a tumor ablation, he is confronted with the risk of having left behind a few tumor cells that are liable to regenerate the tumor or, worse still, migrate to spread disseminated metastases. At the present time, a carcinology surgeon introduces a solution of an antitumor agent into the intraperitoneal cavity that he fills. On closing the operation site, the liquid may spread, which is a major drawback. To avoid the spreading of the liquid, the surgeon often asperates after a relatively short residence time.

The use of poly(N-acryloylglycinamide) makes it possible to solve the abovementioned drawbacks and in particular to obtain a release system that is sufficiently adherent to tissues. Moreover, the use of a gelable aqueous solution in accordance with the present invention has the advantage of making it possible to coat or impregnate a tumor or organs such as the organs of the intraperitoneal cavity, especially during a surgical operation.

Thus, a subject of the present invention is particularly the combination of poly(N-acryloylglycinamide) with at least one antitumor agent, in a physiologically acceptable aqueous medium.

The subject of the invention is also the combination as defined above, which is useful for the local peroperative antitumor treatment of patients who have undergone a tumor reduction surgery. For example, mention may be made of the ablation of a tumor from the intraperitoneal cavity.

A subject of the present invention is also the combination according to the invention for its use in the treatment of wounds, characterized in that it is applied directly to the wound or via any protective device, especially a dressing, for example by impregnation of said protective device with a gel formed from a hot solution.

The combination according to the invention is useful for treating animals, and in particular for treating humans.

In particular, the combination according to the invention is useful in the veterinary field.

The present invention furthermore has the advantage of providing a system that can crosslink in situ, without making use of covalent chemical reactions.

The combination according to the invention may also be injected in liquid and gelable form in situ in a short time so as not to allow diffusion or dispersion beyond the site of administration. Thus, the gelation takes place virtually instantaneously.

In particular, the combination according to the invention gels in a time of less than 5 minutes, preferably less than 3 minutes and better still less than 2 minutes.

The gelation temperature of a combination according to the invention is insensitive to the presence of salt, especially of 0.15N NaCl, and thus to the ionic strength that may be imposed by a parenteral medium.

The injection of the combination may be performed using a conventional syringe and small-aperture needles.

Moreover, the gel form of the combination according to the invention is biocompatible and sterilizable.

Thus, the combination in accordance with the present invention also has the advantage of being stable over time and of allowing its storage up to its application.

The product may thus be stored in gel form and then heated to dissolve it before injection.

The composition may then advantageously be stored in a refrigerator or a freezer, or alternatively in lyophilized form.

Moreover, sterilization may be performed by ultrafiltration of the solution forms through sterilizing ultrafilters (for example 0.22 μm).

Moreover, the combination according to the present invention is particularly advantageous since the hydrogel, once constituted with the aqueous medium, remains stable if an excess of aqueous medium is added. This stability is important more particularly in the delivery of active principles intended for local peroperative antitumor treatment, especially after tumor reduction surgery, since, in situ, the hydrogel is subjected to the neighboring postoperative fluids and exudates, which are more or less abundant depending on the site.

As will emerge in greater detail in the rest of the description, the use of the invention also has an advantage as regards the scope of the possible galenical formulations.

FIGURES

FIG. 1, in relation with example 1, represents the variation of the number-average degree of polymerization $DP_n$ of PAGs obtained as a function of various concentrations of 2-propanol (transfer agent: TA) with a constant concentration of monomer M.

FIG. 2, in relation with example 1, describes the range of critical temperatures according to the concentration of poly(N-acryloylglycinamide).

More precisely, FIG. 2 shows a variation of the phase separation temperatures (gel-sol transition) as a function of the low concentration of PAG observed for PAGs of different average molar masses (from top to bottom: decreasing masses).

FIG. 3, in relation with example 1, shows the range of critical temperatures according to the average molar mass of poly(N-acryloylglycinamide).

More precisely, FIG. 3 shows a variation of the phase separation temperatures (gel-sol transition) as a function of the viscometric molecular mass Mn of PAGs for various concentrations of poly(N-acryloylglycinamide).

FIG. 4, in relation with example 6, shows the curve of release of cobalt acetate in poly(N-acryloylglycinamide) with an average molar mass equal to 170 000 g/mol, as a function of time.

FIG. 5, in relation with example 6, shows the curve of release of poly(sodium acrylate) in poly(N-acryloylglycinamide) with an average molar mass equal to 170 000 g/mol, as a function of time.

FIG. 6, in relation with example 6, shows the curve of release of the poly(tyrosine-formaldehyde) oligomer in poly(N-acryloylglycinamide) with an average molar mass equal to 170 000 g/mol, as a function of time.

DEFINITIONS

The term "gel-sol" means a contraction of the terms "gelation-solution".

The term "hydrogel" means a three-dimensional matrix (physically or chemically crosslinked) swollen with water in aqueous medium.

The term "biodegradable" means a substance or a material which decomposes under the action of live cells, isolated or forming part of a tissue or an organ.

The term "bioresorbable" refers to a substance or material which degrades enzymatically or hydrolytically and for which it is proven that the degradation products are incorporated as biomass and/or removed from the organism aerially after metabolization and/or by renal filtration.

The term "sufficient amount" means a minimum amount that is necessary to achieve the expected effect, for example the reconstitution of a mixture having the properties targeted for the application under consideration.

The term "galenical support for topical application" means a support that is capable of conveying and/or applying an active principle to a site to be treated, for example by formation of a gel temporarily housing said active principle.

The term "UCST" or "upper critical solution temperature" means the maximum temperature above which a polymer-aqueous medium system is in the form of a homogeneous liquid phase. Polymer-aqueous medium systems with an upper critical solution temperature (UCST) are in gelatinous form below the UCST, which form disappears when the temperature is raised above this critical temperature. These polymers owe their insolubility, at a temperature below their UCST, to the presence of reversible intramolecular and intermolecular interactions such as associated ionic or electrostatic interactions.

More precisely, the upper critical solution temperature (UCST) of a polymer-solvent mixture is the temperature above which the components are miscible and the system is a liquid phase that is homogeneous to the naked eye irrespective of the composition of the mixture. In practice, such a polymer-solvent system may be characterized by a reversible gel-sol phase transition which depends on the pressure, the average molar mass and the polydispersity or distribution of the macromolecules of different molar masses ("*Pure and Applied Chemistry*", 2004, 76:1985; Definition of terms related to polymer blends, composites, and multiphase polymeric materials, IUPAC Recommendations, 2004, page 1999).

The term "gel-sol transition temperature" means the temperature above which a given polymer with a UCST in aqueous solution reversibly passes from a hydrogel phase (gel more or less swollen with water) to a liquid phase and thus becomes soluble in the aqueous medium. The reversible gel-sol transition temperature depends on the implementation conditions, for example a single or multiple gel-sol cycle, the rate of cooling or the volume to be cooled.

In the text, the terms "between . . . and . . . ", "ranging from . . . to . . . " and "varying from . . . to . . . " are equivalent and are intended to mean that the limits are included, unless otherwise mentioned.

In the description, the term "at least one . . . " should be understood as meaning "one or more . . . ".

Unless otherwise mentioned, the term "comprising a" should be understood as meaning "comprising at least one".

Polymer

Poly(N-acryloylglycinamide) or PAG or poly(NAGA) is known per se although, apparently, not commercially available.

In reality, the term "poly(N-acryloylglycinamide)" or its abbreviations denote a family of macromolecular compounds which differ by their mass-average and number-average molar masses and by the dispersity thereof reflected by the polydispersity index or the polydispersity defined by the ratio of the mass-average molar mass to the number-average molar mass.

The macromolecules of PAG type have the formula (I) below:

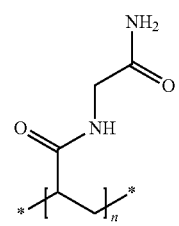

(I)

In the context of the present invention, the average molar mass of the PAG is preferably between 10 000 and 1 000 000, more particularly between 30 000 and 600 000, or even between 40 000 and 200 000 g/mol.

According to a particular embodiment, the average molar mass is evaluated by viscometry, for example as detailed in example 1 below.

In the same manner as in the examples, the viscometric values may be measured using an Ubbelohde viscometer.

This polymer in solution is a heat-sensitive polymer. In the case of PAG, the heat-dependent crosslinking takes place by formation of a network of hydrogen bonds between the NH and C=O groups present in the side chains of glycinamide type rich in interactive functional groups. The PAG hydrogels are said to be dependent on an upper critical solution temperature phenomenon (UCST or solution at high temperature and gel at low temperature).

PAG hydrogels are occasionally known as "artificial gelatin".

More particularly, PAG polymer, mixed with an aqueous medium, may lead to a solution (sol) or hydrogel (gel) depending on the temperature of said medium.

The basic interest of this polymer as a source of smart hydrogel is that, when mixed with an aqueous medium it may lead to a solution (sol) or a hydrogel (gel) depending on the temperature and that the gel-sol transition may be brought into the temperature zone of an animal organism such that, when administered in sol form at a temperature that is higher but compatible with that of the organism under consideration (human or animal), it becomes gelled when the administered sol returns to the latter temperature.

In the context of the present invention, the poly(N-acryloylglycinamide) copolymers may also be considered with various monomers as described in "*Synthetic thermally reversible gel systems*", Haas et al., Journal of Polymer Science, Polymer Physics Edition, II, 1967, Vol. 5, 5:915. Such monomers may be chosen in particular such that the solutions of these copolymers satisfy the conditions imposed by the animal and/or human organisms.

A person skilled in the art is capable of synthesizing the polymer that is suitable for use in the invention according to his general knowledge. The polymerization (and the optional copolymerization) may be initiated in bulk or in solution in an organic solvent with free-radical generators. Initiators of anionic and cationic type may also be used on condition that this is suitable for obtaining a PAG having a gel-sol transition temperature.

For example, the polymer that is suitable for use in the invention may be prepared according to the protocol described in the articles published by Haas, especially in "*Synthetic thermally reversible gel systems*", Haas et al., Journal of Polymer Science, IV, Part A-1, Polymer Chemistry, 1970, Vol. 8, 5:1213.

In the context of the present invention, polymerization by radical initiation via chemical decomposition will be preferred with the use of initiators that generate radicals at elevated temperature such as benzoyl peroxide, tert-butyl peroxide, diazo compounds such as azobisisobutyronitrile, peroxygenated compounds such as persulfates or aqueous hydrogen peroxide solution, redox systems such as the oxidation of $Fe^{2+}$ or of $Ce^{4+}$, persulfate/sodium metabisulfite mixtures, or ascorbic acid/hydrogen peroxide or alternatively compounds that can be cleaved photochemically or with ionizing radiation, for example by UV or by beta and gamma rays.

According to a particular embodiment, the polymer that is suitable for use in the invention is prepared via a radical polymerization method.

In order to control the average molar masses, as is more particularly illustrated in example 1, a transfer agent may be used.

For example, the production of more or less high average molar masses may take place by using transfer agents as described in Haas et al., Journal of Polymer Science, 1964, Vol. 2, 12:1095 and more recently in "*Well-defined synthetic polymers with a protein-like gelation behavior in water*", Glatzel et al., Chemical Communications, 2010, 45, 4517.

The purpose of the transfer agent is to stop the growth of the macromolecular chains that are under formation by addition of monomer molecules and of new chain initiator, which makes it possible to limit the final molecular masses, or even to control them.

In the context of the present invention a transfer agent may be chosen more particularly from thiols such as dodecylthiol $C_{12}H_{25}SH$ or thioglycolic acid $HSCH_2COOH$, halogenated derivatives such as $CHCl_3$ or brominated derivatives, or alcohols such as isopropanol, as indicated in U.S. Pat. No. 3,396,030.

PAGs with different average molar masses may also be obtained from a PAG by triangle fractionation using a solvent-nonsolvent mixture, for example, according to a standard method in polymer sciences, which is well known to those skilled in the art.

Gel-Sol Transition Temperature

In the context of the present invention, gel-sol transition temperature is advantageously at a temperature above body temperature, such that the system is in solution form (sol) at a temperature above body temperature, but below the maximum temperature that may be supported by tissues, namely 60° C., preferably 50° C., and is in a hydrogel form (gel) at the body temperature of the site of administration, generally 37° C. in the case of a man, or a different value in the case of animals, and in any case between 35° C. and 42° C.

Thus, according to a particular embodiment, the combination according to the invention has a gel-sol transition temperature of between 30 and 60° C., or even between 38 and 50° C. and better still between 35 and 45° C., which is measured, for example, via the inverted tube method.

The gel-sol transition temperature is readily adaptable, if need be, as regards the temperature of the site to be treated. In particular, it is possible to modulate the gel-sol transition temperature by varying diverse parameters.

Specifically, the gel-sol transition temperature of a given mixture comprising a given polymer depends on macromolecular factors such as the average molar mass, the molar mass distribution, the presence of any comonomers, the concentration of the polymer in the aqueous solution, the salinity, and also the presence of additives, especially hydrophobic compounds, including the active principles.

For example, the gel-sol transition temperature is especially dependent both on the concentration and average molar mass of the polymer. Increasing one of these two adjustment variables has the effect of increasing the intra-chain and inter-chain interactions, thus increasing the gel-sol transition temperature.

In practice, these two parameters may advantageously be used to obtain a polymer that is in accordance with the requirements in terms of gel-sol transition temperature, as illustrated in example 1.

As regards the link between the gel-sol critical transition temperature, the average molar mass and the concentration of the polymer in the aqueous solution, reference may be made in particular to FIG. 1, which shows the range of gel-sol transition temperatures according to the average molar mass and the polymer concentration.

The presence of salt, especially from the medium constituting the physiological liquid whose ionic strength and pH are compatible and imposed with biological fluids, does not significantly impair the behavior of a given PAG, which is a neutral polymer, observed in water, especially the ability to form a gel.

The presence of a hydrophobic or hydrophilic compound in a formulation may modify the gel-sol transition temperature observed in their absence. However, it is possible to compensate for the effect by modifying the parameters intrinsic to the polymer, such as the average molar mass and the concentration.

Methods for Measuring the Gel-sol Transition Temperature

The gel-sol transition temperature value depends on the technique used for its determination.

For example, the inverted tube method, the falling ball method or a dynamic viscosity measurement may be used.

In the context of the present invention, the gel-sol transition temperature may be measured via the inverted tube method.

The principle of the inverted tube method consists in gelling a PAG-based solution in a glass tube equipped with a thermometer fixed via a stopper, inclining the tube head downward and raising and then lowering the temperature of the assembly gradually, noting the temperatures at which the material begins to flow by simple gravity during the increase and/or when the medium sets during the decrease.

More particularly, dried poly(N-acryloylglycinamide) is placed in a 20 $cm^3$ glass tube with deionized water. The mixture is placed in a water bath at 80° C. until totally dissolved. The solution is then cooled to room temperature and gelled.

The system is returned to 80° C. for 5 minutes, and then cooled to 0° C. at a rate of 40° C./minute, left at 0° C. for 30 minutes and then heated to 80° C. at a rate of 4° C./minute.

A first gel-sol transition temperature is determined when the gel begins to flow along the wall of the tube. This cycle is repeated 3 times to give four gel-sol temperatures.

A reproducibility of ±2° C. of the gel-sol transition temperature is generally observed after the second cycle.

Active Principle and Product Visible in Medical Imaging

Active Principles

As active principles that may be suitable for use in the present invention, mention may be made in particular of antitumor agents, antibiotics, analgesics, anti-inflammatory agents, growth factors and antiseptics.

Among the antibiotics, the ones that are especially suitable for use in the invention are those of the class of aminoglycosides, such as gentamicin or kanamycin; ansamycins; carbacephems; carbapenems; first-generation cephalosporins, such as cefadroxil or cefazoline; second-generation cephalosporins, such as cefaclor or cefamandole; third-generation cephalosporins, such as cefixime; fourth-generation cephalosporins; fifth-generation cephalosporins, such as ceftobiprole; glycopeptides; lincosamides; lipopeptides; macrolides; monobactams; nitrofurans; penicillins, such as amoxicillin or ampicillin; combinations of penicillins; polypeptides; quinolones, such as ciprofloxacin or ofloxacin; sulfonamides, such as sulfadiazine or sulfadiazine silver; tetracyclins, such as oxytetracyclin or tetracycline; antibiotics that are useful against mycobacteria; or alternatively metronidazole or thiamphenicol.

Among the analgesics that are more particularly suitable for use in the invention, mention may be made especially of buprenorphin, fentanyl or ibuprofen.

The antiseptics that are suitable for use in the invention may be chosen more particularly from hexomedine, silver salts and iodine.

Among the growth factors that are suitable for use in the invention, mention may be made most particularly of FGFa and FGFb, VGOF and GRF.

Preferably, mention may be made especially of any active principle with antitumor activity. Among these active principles, mention may be made more particularly of doxomubicin, paclitaxel, topotecan and irinotecan.

Radioactive compounds may also be mentioned for internal radiotherapy, in particular grains of iodine-125, which are used especially in the treatment of prostate cancer.

Moreover, the abovementioned active principles may be formulated, where appropriate, in the form of microparticles or nanoparticles that are preferentially bioresorbable so as to be trapped in the gel. Similarly, the active principle may be in the form of vector-active principle polymer conjugates, conventionally known as macromolecular prodrugs.

Several active principles of different nature may be administered simultaneously by means of the solution in accordance with the present invention. This polyvalency is particularly advantageous for multi-resistant tumoral sites. The advantage is readily extended to the temporary trapping of peptides, proteins, genes and molecules which, in general, pose a problem on account of their exclusive solubility in aqueous media and which, in the case of matrix or capsule particulate systems, often bring about an excessively rapid and unsuitable release and generally mobilize a large amount of foreign material to the living medium relative to that involved in PAG-based formulations.

Products that are Visible in Medical Imaging

The combination according to the invention may also comprise at least one product that is visible in medical imaging.

As product that is visible in medical imaging, mention may be made most particularly of opacifiers, such as an oxide or a mineral salt, for example barium sulfate or zirconium oxide to allow X-ray monitoring, magnetic particles or paramagnetic nanoparticles for disruption with a magnetic field.

Mention may also be made of fluorescent agents or ionizing radiation emitters, to make the hydrogel visible via the corresponding appropriate techniques.

Preferably, the product that is visible in medical imaging is chosen from an opacifier, a fluorescer and an ionizing radiation emitter.

According to an embodiment variant, the combination according to the invention comprises poly(N-acryloylglycinamide), at least one active principle and at least one product that is visible in medical imaging, in a physiologically acceptable aqueous medium.

Physiologically Acceptable Aqueous Medium

The physiologically acceptable aqueous medium according to the invention is preferably prepared based on a physiological liquid.

A physiological liquid is a liquid that is isotonic to blood, i.e. having the same osmolarity as the main bodily fluids, in particular blood, i.e. about 300 mosm/L and generally buffered at pH=7.4.

Such a liquid may also be referred to as a physiological solution or physiological serum.

This liquid is generally composed of distilled water and sodium chloride NaCl diluted to 9 per 1000, i.e. a solution at 0.9% by weight/volume of NaCl, i.e. 9 g/L.

The physiological liquid may also contain KCl, $CaCl_2$ or $MgSO_4$.

The term "physiologically acceptable medium" generally means a medium that is free of toxicity and compatible with the injection and/or application of the combination under consideration according to the invention. In particular, it means a medium that is compatible with the fluids, tissues and cells of the site of application under consideration.

Combination According to the Invention

As already outlined above, the combination according to the invention comprises poly(N-acryloylglycinamide) and at least one active principle and/or at least one product that is visible in medical imaging, in a physiologically acceptable aqueous medium.

According to a particular embodiment, poly(N-acryloylglycinamide) is present in the aqueous medium in a solids content of between 0.5% and 20% by weight, relative to the total weight of said medium, in particular in an amount of between 1% and 10% by weight, or even more particularly between 2% and 8% by weight.

The combination according to the invention may also comprise additives, especially hydrophobizing agents such as a lipid, a fatty acid or a fatty amine.

PAGs, which are endowed with a polyacrylic backbone, are not intrinsically degradable and/or biodegradable, and even less so bioresorbable. However, the amounts administered are generally very low and the risks of accumulation are themselves low since the polymer contents that are administered remain very low, for example between 2% and 8% by weight relative to the total weight of the composition under consideration, so as to satisfy the gel-sol transition temperature range targeted in the context of the present patent application and imposed by the live medium.

Moreover, it is possible to obtain a PAG that has improved biodegradability properties by adding a slightly basic insoluble additive such as MgO or CaO. However, it is possible to alter the side chains in the presence of particles of a more or less basic insoluble compound (for example CaO, $Ca(OH)_2$, MgO, $Mg(OH)_2$, etc.) capable of totally or partially hydrolyzing the amide functions present, and thus of minimizing the crosslinking interactions that are the source of the gelation to arrive at soluble forms.

Without being bound by theory, it may be assumed that the bases added cleave the side chains to leave poly(N-acryloylglycine) and probably (poly(acrylic acid-co-N-acryloylglycinamide-co-N-acryloylglycine) copolymers or alternatively poly(acrylic acid-co-N-acryloylglycine) copolymers that are soluble, or even poly(acrylic acid) in salt form.

Thus, example 3 below bears witness to this phenomenon, which may be exploited to adjust the desired time of presence on site in the organism and/or on the wound.

The formation of soluble macromolecules on site is particularly advantageous if their average molar masses are low enough for them to be able to be removed by glomerular filtration in the kidneys.

As mentioned previously, the combination described above is in the form of an aqueous formulation comprising the polymer in solution form (sol) when it is at a temperature above the gel-sol transition temperature of the mixture under consideration.

A hot aqueous solution of PAG at a temperature a few degrees higher than the temperature of the site of administration takes little time to pass from the sol state to the gel state when it is placed in contact with the human body, especially between 10 seconds and 5 minutes and more particularly between 30 seconds and 3 minutes.

The solution may be prepared extemporaneously, gelled and sterilized locally by ultrafiltration while hot after fluidization by heating just before application, if necessary or preferred.

Alternatively, the mixture may be prepared in advance in dehydrated form after lyophilization of a sterilized or non-sterilized hot solution for the purpose of conserving it. After heating, the solution comprising the polymer and the active principle may be sterilized by ultrafiltration, if necessary, and packaged after lyophilization, for example, for the purpose of conserving it. The chemical stability of the polymer in accordance with the present invention offers a possibility of long storage without any particular precautions, which is not the case for degradable matrix systems based on PLA or PLA-PEG copolymers, in particular.

Thus, according to one embodiment variant, the present invention also relates to a lyophilizate prepared from an aqueous solution of poly(N-acryloylglycinamide), and optionally of at least one active principle and/or at least one product that is visible in medical imaging and optionally an additive.

The present invention also relates to the process for preparing a lyophilizate as defined above, characterized in that it comprises at least the following steps:
the preparation of a gelable aqueous solution of poly(N-acryloylglycinamide);
sterilization of said solution;
gelation of said solution by cooling;
freezing of the hydrogel; and
sublimation of the ice as water vapor, under vacuum.

According to another embodiment variant, the present invention relates to a lyophilizate prepared from a solution of poly(N-acryloylglycinamide) and of at least one active principle and/or at least one product that is visible in medical imaging.

The present invention also relates to the process for preparing a lyophilizate as defined above, characterized in that it comprises at least the following steps:
the preparation of an aqueous solution of poly(N-acryloylglycinamide) and of at least one active principle and/or at least one product that is visible in medical imaging;
sterilization of said solution;
gelation of said solution by cooling;
freezing of the hydrogel; and
sublimation of the ice as water vapor, under vacuum.

Applications

The combination according to the invention is particularly useful for delivering an active principle, especially in human and veterinary therapy.

As an application targeted in the context of the present invention, mention may be made especially of local treatment by topical controlled delivery of active principle.

More particularly, mention may be made of the complementary local treatment of a surgical ablation that is liable to leave pathogens or proliferative cells present locally or after migration, as is the case for residual tumor cells in certain cancers.

Thus, the local delivery of active principles at the tumor site via the intraperitoneal cavity (ip) exposes the residual cancer cells to higher doses than those that may be obtained by systemic chemotherapy, while at the same time minimizing the side effects.

The aqueous solution in accordance with the present invention may be readily injected, alternatively to intraperitoneal administration, directly into or on immediate contact with a tumor to become a deposition phase, according to the will of the clinical user.

Thus, in the context of the present invention, the combination is more particularly useful for local post-operative or peroperative treatment, especially of patients who have undergone a tumor reduction surgery.

More specifically, the combination according to the invention is useful in local peroperative antitumor treatment after tumor reduction surgery.

The term "local peroperative treatment" means a topical treatment applied around the region of the animal body and more particularly the human body, which has undergone ablation of a tumor part.

Moreover, in the context of the present invention, the combination is useful for treating wounds, where it may be either applied directly to the wound or via any protective device, especially a dressing, for example by impregnation of said protective device by soaking in the aqueous formulation in the form of a hot solution and cooling leading to a dressing coated with gel.

If need be, in the event of a removal made difficult by excessively strong adhesion, brief heating of the reticent dressing to return the gel to a sol may be performed to facilitate the detachment of the dressing.

According to another aspect of the invention, the combination is also useful for post-operative monitoring by medical imaging.

The combination according to the invention may be useful for treating animals, in particular humans.

The combination according to the invention may also be useful in many other fields in which sustained-release forms of active compounds are exploited, such as in cosmetics (hair-removing creams, acidic skin erosion agents, etc.) or in agriculture (treatment of plants, beehives, etc.).

The administration may involve a galenical formulation in the form of a solution that is gelable in situ. The same formulation may also be administered in the form of powder derived from a lyophilization, especially as described above, this powder swelling by taking up water from the local biological fluids. It is also possible to administer the hydrogel itself by injection, provided that its viscosity allows it.

The aqueous solution in accordance with the present invention may, for example, also be applied directly by sprinkling.

It is possible either to use an instrument (brush, spatula or comb) to spread the sol phase onto a site, or to inject the sol phase using a controlled heating syringe, or alternatively to disperse a formulated lyophilizate powder.

The subject of the present invention extends to any galenical support for topical application comprising a combination in accordance with the present invention.

Kit and Packaging

According to another aspect, the present invention relates to a kit or packaging assembly, comprising a container comprising a formulated gel to which will be added a given amount of sterile physiological liquid before heating to obtain a hot solution.

The term "sterile" is intended to qualify an environment that is capable of ensuring the required harmlessness.

Alternatively, the kit may comprise at least two separate containers or two separate compartments in the same container, one comprising a prepared lyophilizate based on poly(N-acryloylglycinamide), and the other comprising a sufficient amount of sterile physiological liquid making it possible to reconstitute the initial mixture by mixing with said lyophilizate and heating to obtain a hot solution.

The user may thus reconstitute a composition according to the invention, by extemporaneously mixing, just before application, the various constituents of the kit.

For example, according to a particular embodiment, a multi-compartment and more particularly two-compartment bag may be provided.

Thus, the bag may have at least two compartments that are isolated from each other by a membrane that is leaktight but fragile enough to be torn under the action of a compression, each compartment being intended to store at least one compound that is useful for manufacturing a solution in accordance with the invention.

According to a first alternative, the bag is a two-compartment bag, the first compartment comprising at least sterile physiological serum, and the second compartment comprising at least one lyophilizate of poly(N-acryloylglycinamide).

According to a second alternative, the bag is a three-compartment bag, each compartment possibly being dedicated, respectively, to the packaging of lyophilizate of poly(N-acryloylglycinamide), of sterile physiological serum and of at least one active principle to be delivered and/or of at least one product that is visible in medical imaging.

In these embodiments in which the various compounds may advantageously be isolated from each other in respective compartments, a first step then involves preliminary breaking of the membrane separating the compartments, for example by means of a simple pressure.

According to yet another aspect, the present invention relates to a bottle, comprising at least one mixture prepared from an aqueous solution of poly(N-acryloylglycinamide) and optionally of at least one active principle and/or of at least one product that is visible in medical imaging, and having a septum for withdrawing said mixture after heating the bottle, for example using a syringe which is itself heating or heated.

The embodiments described above make it possible to dispense with any step necessitating contact of the composition with the external environment, consequently significantly reducing the risks of contamination.

The examples below illustrate the present invention without limiting its scope.

EXAMPLE 1

Synthesis of the Acryloylglycinamide (AG) Monomer 113.62 grams (1.03 mol) of glycinamide hydrochloride are dispersed in 700 ml of dichloromethane in a glass reactor, dipped in an ice bath, equipped with a mechanical stirrer (at 500 rpm) and a thermometer.

When the temperature reaches about 5° C., 100 ml of acryloyl chloride (1.23 mol) are added rapidly. 565 ml of 2M potassium carbonate solution are then added dropwise so that the temperature does not exceed 20° C. At the end of the addition, the pH of the aqueous phase is about 7-8 (measured on pH paper). Stirring is continued for 2 to 3 hours at room temperature.

The aqueous phase is separated out, passed through active charcoal, filtered and immediately lyophilized. 290 g of a mixture consisting essentially of AG and of potassium chloride KCl are recovered and finely ground.

The AG is extracted from this mixture with 16 fractions of 500 ml of acetone, and each fraction is placed for 5 to 15 minutes in an ultrasonication tank.

In a first experiment, 93.7 g of crude AG are recovered (the crude yield is 70%) and recrystallized from 3 liters of acetone. After washing with acetone, the AG is dried under vacuum (<0.01 mbar) at 35° C. for two days.

The recrystallization yield is 68%.

In a second experiment, the 93.7 g of crude AG are recovered (the crude yield is 70%) and recrystallized from 800 mL of an acetone/methanol mixture (9:1 by volume). After washing with acetone, the AG is dried under vacuum (<0.01 mbar) at 35° C. for two days.

The recrystallization yield is 20%.

$^1$H NMR (D$_2$O); δ (ppm) 6.06 (2H, CH$_2$=C); 5.60 (1H, CH=C), 3.76 (2H, CH$_2$CO).

$^{13}$C NMR (D$_2$O): δ (ppm) 175.5 (CO—NH$_2$); 169.0 (CO—NH); 129.9 (CH$_2$=CH); 128.6 (CH=CH$_2$); 42.5 (CH$_2$NH).

Analysis calculated for C$_5$H$_8$N$_2$O$_2$: C, 46.87; H, 6.29; N, 21.86; O, 24.97.

Analysis measured for C$_5$H$_8$N$_2$O$_2$: C, 46.96; H, 6.29; N, 21.74; O, 25.01.

Melting point: 126-127° C.

Polymerization of N-acryloylglycinamide (AG)

The radical polymerization of AG in aqueous solution is performed at a constant AG monomer concentration and a constant initiator K$_2$S$_2$O$_8$ concentration: [AG]=0.5 mol/L and [K$_2$S$_2$O$_8$]=5×10$^{-4}$ mol/L. The concentration of 2-propanol (transfer agent, TA) ranges between 0 and 4 mol/L.

The AG, the K$_2$S$_2$O$_8$ (redox initiator), the TA and water are introduced into a 150 mL glass tube. The reaction medium is degassed by circulating a stream of argon through it for about 1 hour. The tube under argon is placed in a water bath thermostatically maintained at 60±0.2° C. for 24 to 26 hours.

Two methods for recovering the poly(acryloyl glycinamide) (PAG) are used depending on the TA concentration:

1) For a concentration [TA]>1.5 mol/L, the reaction mixture is dialyzed against water using a Spectrapore membrane (cutoff power M$_W$=3500) and lyophilized;

2) For a concentration [TA]<1.5 mol/L, the PAG is precipitated in 6 volumes of methanol using a mixer (Waring Blendor) and then washed with methanol and dried under vacuum at 50° C. for 2 to 3 days.

The yields are between 80% and 90%.

$^1$H NMR (D$_2$O—NaSCN 2M): δ (ppm) 4.00 (2H, CH$_2$—CO); 2.32 (1H, CH—C); 1.72 (2H, CH$_2$—C).

$^{13}$C NMR (D$_2$O—NaSCN 2M): δ (ppm) 177.8 (CO—NH$_2$); 174.5 (CONH); 134.0 (SCN); 42.9 (CH$_2$—NH); 35.9 (2C, CH$_2$CH).

The polymers obtained are characterized by $^1$H NMR and $^{13}$C NMR, for example with a Brüker spectrometer (100 MHz). The melting points are measured on a Köfler bench.

The viscometric measurements are taken at 25° C. on an Ubbelhode automatic machine or an automatic viscometer.

Table 1 below presents data relating to the radical polymerization of AG ([AG]=0.5 mol/L) in aqueous solution at 60° C. initiated with potassium persulfate ([$K_2S_2O_8$]=5×10$^{-4}$ mol/L) for various concentrations of transfer agent (2-propanol).

TABLE 1

| PAG No. | [2-propanol] in mol/L | [η] (dl/g) $H_2O$—NaSCN 2M at 25° C. | Mn ×10$^{-3}$ |
|---|---|---|---|
| 1 | 0 | chemical gel | — |
| 2 | 0.16 | 1.12 | 549 |
| 3 | 0.30 | 0.91 | 369 |
| 4 | 0.43 | 0.69 | 216 |
| 5 | 0.69 | 0.62 | 176 |
| 6 | 0.98 | 0.42 | 83 |
| 7 | 1.20 | 0.40 | 79 |
| 8 | 1.66 | 0.28 | 38 |
| 9 | 2.00 | 0.26 | 33 |
| 10 | 3.33 | 0.20 | 20 |
| 11 | 3.99 | 0.18 | 16 |

The synthesis of PAGs Nos. 5, 6 and 9 were repeated with the same operating conditions. The PAGs obtained have respective viscosities of 0.55, 0.39 and 0.29 dl/g, corresponding, respectively, to viscosimetric Mn values of 140, 72 and 41×10$^{-3}$.

These duplications show that the differences are of the order of 10% to 15%. These values are tolerable given the accuracy of the average molar mass determinations by viscometry.

The following equation (according to C. A. *Barson in Comprehensive Polymer science*, Vol. 3, *Chain Polymerization I*; Pergamon Press, New-York, 1989, p. 173) may be used for the determination of the 2-propanol transfer constant:

$$1/DP_n = 1/DP_0 + C_M + C_S[S]/[M] + C_I[I]/[M] + C_{TA}[TA]/[M]$$

in which:
DP$_0$ represents the number-average degree of polymerization DP$_n$ in the absence of transfer reactions;
$C_M$, $C_I$, $C_S$ and $C_{TA}$ are the transfer constants for the monomer M, the initiator I, the solvent S and the transfer agent TA;
[S]=the concentration of solvent;
[I]=the concentration of initiator;
[M]=the concentration of monomer, and
[TA]=the concentration of transfer agent.

FIG. 1 shows the variation in the number-average degree of polymerization DP$_n$ for the PAGs obtained at 60° C. (□) and at 75° C. (■) as a function of the concentration of 2-propanol (transfer agent: TA). The concentration of monomer M is constant: [M]=0.5 mol/L (□) and 0.75 mol/L (■).

When the concentrations of monomer M and of initiator I are constant and when the low variation in solvent concentration relative to the concentration of TA (34.5<[$H_2O$] (mol/L)<54.5) is ignored, the 2-propanol transfer constant may be estimated by following the linear variation of 1/DP as a function of the ratio [TA]/[M].

This variation is represented in FIG. 1 in the case of the PAGs obtained, described in the above table, at 60° C. and for the PAGs obtained at 75° C.

The DP values are calculated from the viscometric measurements in 2M $H_2O$—NaSCN at 25° C.

NaSCN destroys hydrogen bonds and prevents gelation at room temperature, so as to perform the characterization.

The experimental points are dispersed about a straight line. The respective mean equation is:

$1/DP_n=1.02$ [TA]/[M]$-3.94\times10^{-1}$ (the correlation coefficient is $R^2=0.988$) at 60° C.; and $1/DP_n=1.04$ [TA]/[M]$-4.94\times10^2$ (the correlation coefficient is $R^2=0.999$) at 75° C.

The y-axis at the origin tends toward 0 and suggests a very high DP$_0$, greater than 10$^5$.

The slopes of these straight lines make it possible to estimate the 2-propanol transfer constant: $C_{TA}=1.02\times10^{-3}$ at 60° C. and $C_{TA}=1.04\times10^{-3}$ at 75° C.

These values are of the same order of magnitude as the 2-propanol transfer constant in the case of the radical polymerization in aqueous solution at 50° C. of acrylamide: $C_{TA}$ 1.9×10$^{-3}$.

The gel-sol transition temperature of the PAG gels in water was determined in the following manner:

Starting with dry PAG powder, 10 g of suspensions with concentrations C of 2%, 4%, 6%, 8% and 10% by weight in water are prepared in 20 ml test tubes.

Since the gelation phenomenon is subject to hysteresis, several gel-sol cycles were performed in order to obtain a reproducible gel, according to the following recycling procedure:

The suspensions are heated at 80° C. for 2 hours and then cooled to room temperature.

The sol phase is reformed by heating at 80° C. for 5 minutes.

A first gel-sol transition temperature is determined.

The sol is then cooled to 0° C. in water and ice.

After a time of 30 minutes, the gel is raised slowly, at a rate of 4° C./minute, to 80° C.

A new gel-sol transition temperature is recorded.

The gel is again cooled to 0° C. over 30 minutes.

Two new similar cycles are engaged.

The four temperatures observed are indicated for each polymer and concentration in Table 2. The reproducibility appears to be good at and above the third cycle, and occasionally at and above the second.

Table 2 below shows the influence of successive hot-cold cycles on the gel-sol transition temperature T$_{gel/sol}$, on formulations with a concentration C of PAG of molar mass Mn.

The molar mass Mn is determined by viscometry at 25° C. in water in the presence of 2M NaSCN, by applying the viscosity law [η]=1.16×10$^3$ Mn$^{0.52}$ according to H. C. Hass, R. I. MacDonald and A. N. Schueler, J. Polym. Sci., Part A1, 1970, 8, 1213.

TABLE 2

(on 4 cycles)

| Concentration C (mass %) | Mn = 549 × 10$^3$ (100 cm$^3$/g) | Mn = 176 × 10$^3$ (100 cm$^3$/g) | Mn = 79 × 10$^3$ (100 cm$^3$/g) | Mn = 41 × 10$^3$ (100 cm$^3$/g) |
|---|---|---|---|---|
| 2 | 59/61/57/57 | a) | a) | a) |
| 4 | 64/75/70/70 | 52/57/50/50 | a) | a) |
| 6 | 80/80/80/80 | 59/64/62/62 | 35/50/48/49 | 32/36/35/35 |
| 8 | b) | 67/72/70/68 | 55/60/58/58 | 46/52/48/48 |
| 10 | b) | 70/75/75/73 | 60/63/64/63 | 52/56/55/55 | a) no formation of gel at 25° C. and at 0° C.
b) not determined

It may be deduced from Table 2 that the PAGs of Mn=549×10$^3$ at C=2%, of Mn=176×10$^3$ at C=4% or 6%, of Mn=79×10$^3$ at C=6% or 8%, and of Mn=41×10$^3$ at C=6% or 8% or 10% will be particularly considered in the context of the present invention (shaded parts).

EXAMPLE 2

Figure 1:
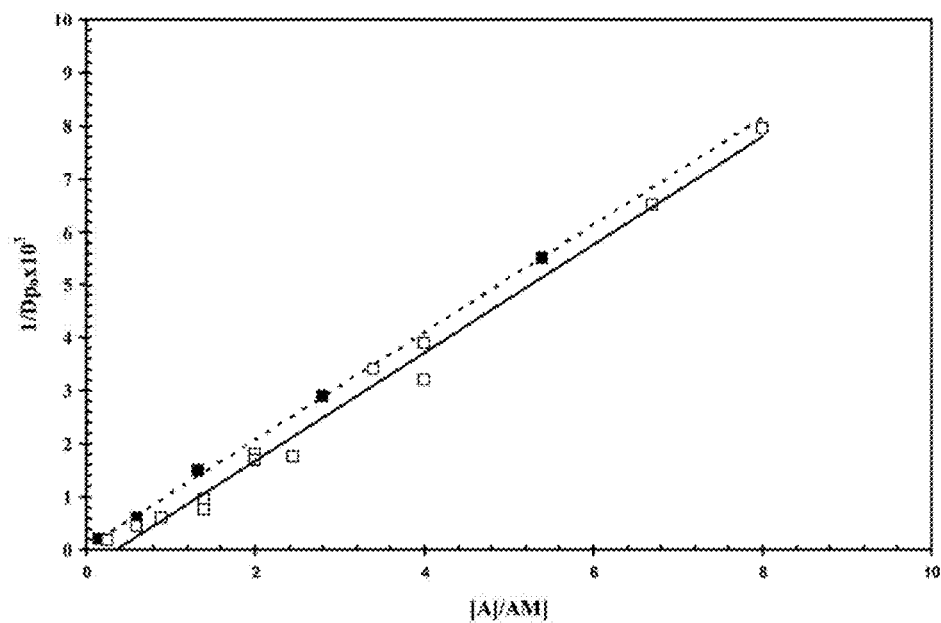
Figure 2:
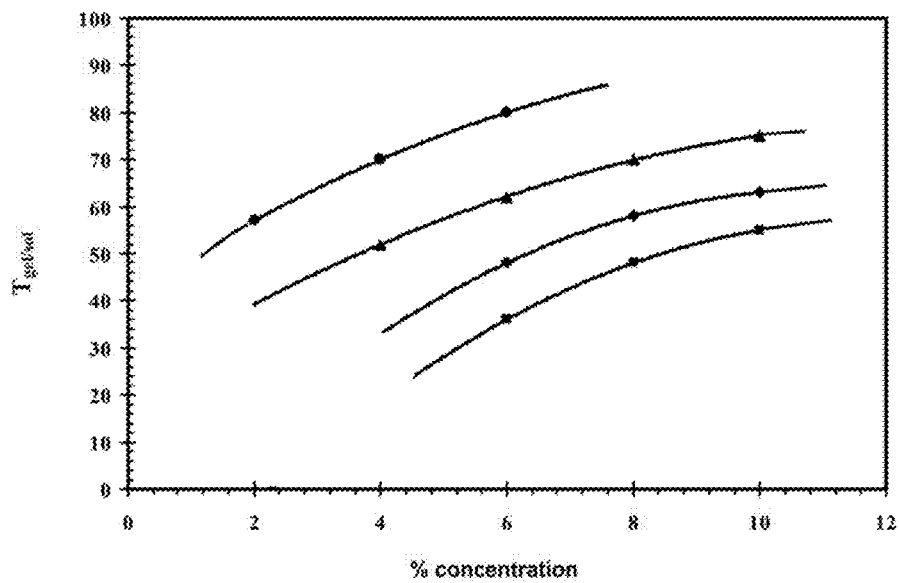
FIG. 2 shows the variation in the gel-sol transition temperature $T_{gel-sol}$ as a function of the concentration for PAGs with molecular masses $Mn \times 10^{-3} = 41$ (■), 76 (♦) and 549 (●).
Figure 3:
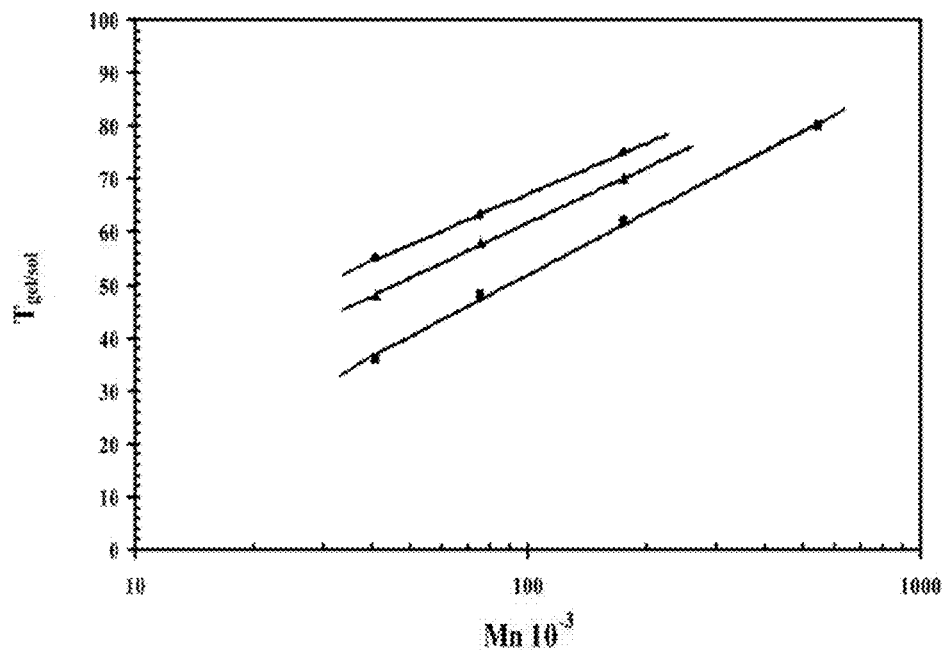
FIG. 3 shows a variation of the phase separation temperatures (gel-sol transition) as a function of the molecular mass Mn of the PAGs for concentrations C of 6% (■), 8% (▲) and 10% (●).

Four normal mice 1 to 4, treated according to the ethical rules in force, were operated on by opening the peritoneal cavity as a preliminary step, and received 1 ml of blank solution (1, 2, 3 or 4) combining a PAG (369 000 g/mol) and doxorubicin, administered using syringes heated with hot air.

Preparation of solution 1 for mouse 1: 100 mg of PAG No. 3 of example 1 in powder form are placed in a conical flask. 4 ml of physiological serum are added thereto. The mixture is gradually heated to reach a dissolution temperature with formation of a homogeneous medium at 60-65° C. The mixture, cooled but remaining in solution, is administered to the intraperitoneal cavity of mouse 1 and left gelled on site for 2 minutes until gelation at 37° C. The mouse's abdomen is closed up with a few stitches.

Preparation of solution 2 for mouse 2: Solution 2 is prepared according to the same procedure as solution 1, with the following amounts: 25 mg of PAG No. 3 and 4 mg of doxorubicin hydrochloride (Dox) in 4 ml of physiological serum are introduced after the formation of the homogeneous medium.

Preparation of solution 3 for mouse 3: Solution 3 is prepared according to the same procedure as solution 1, with the following amounts: 100 mg of PAG No. 3 and 4 mg of doxorubicin hydrochloride (Dox) in 4 ml of physiological serum are introduced after the formation of the homogeneous medium.

Preparation of solution 4 for mouse 4: Solution 4 is prepared according to the same procedure as solution 1, with the following amounts: 100 mg of PAG No. 3 and 0.8 mg of doxorubicin hydrochloride (Dox) in 4 ml of physiological serum are introduced after the formation of the homogeneous medium (therapeutic concentration).

During the administration of the non-gelling mixture to mouse 2, the operator observed leakage of the solution during the closure of the cavity, which is a drawback that is well known to clinicians when they use solutions of antitumor agent.

After two days, mice 2 and 3, which are alive but badly affected by the strong dose of Dox, were sacrificed. The intraperitoneal cavity of mouse 2 appeared empty. Mouse 3 appeared virtually normal with only a few traces of gel in the form of small pieces wedged in the crevices.

It appears that a large part of the gel has at least visually disappeared.

The two other mice 1 and 4 were still alive after 4 days and neither appeared to be affected by the presence of the gel or of the gel-Dox.

EXAMPLE 3

Mixtures for Testing the Partial Degradability of Salified PAG to PAA (Poly(Acrylic Acid))

40 mg of PAG No. 3 are placed in contact with 1 ml of water in a flask heated to 80° C. so as to have a clear solution, and the solution is gelled by cooling and subjected to two new hot-cold cycles (as described in example 1) to obtain a homogeneous gel.

4.5 mg of a finely sprayed mineral ($BaSO_4$, $Ca(OH)_2$, $Mg(OH)_2$ or $Na_2CO_3$) are added and the gel-mineral mixture is redissolved while hot and the dispersion is homogenized using a homogenizer and cooled with stirring to give a homogeneous dispersion of salt in the gel after cooling.

The various flasks are then placed in an incubator maintained at 37° C.

Depending on the mineral, the following are observed:

for $BaSO_4$ (barium sulfate), opacity of the gel and stability of the gel over 5 weeks;

for $Ca(OH)_2$ (calcium hydroxide), which is a very sparingly soluble weak base, the medium is still gelled after 5 weeks;

for $Mg(OH)_2$ (magnesium hydroxide), which is a sparingly soluble weak base, the gel loses its viscosity after 4 days. After 2 weeks, the gel has left in its place a very viscose solution; and for $Na_2CO_3$, which is a stronger base, the gel liquefies from the second day and gradually leaves in its place a clear, viscose solution.

This example is directed toward illustrating the modulation that may be performed in order to adjust the "solubilizing degradability" of the PAGs under consideration.

EXAMPLE 4

Combination comprising an opacifier

The same protocol as for the basic products of example 3 is used to obtain a gel containing 10% by weight of barium sulfate or zirconium oxide.

Such a concentration of these agents is used in order to make X-ray opaque orthopedic cements.

The corresponding hydrogels are then detectable by X-ray, which makes it possible to monitor their fate in situ.

EXAMPLE 5

Combination Comprising Paramagnetic Nanoparticles

The same protocol as for examples 3 and 4 is applied to 100 µl of sol and 2 mg of paramagnetic nanoparticles (PMN) of 5 to 200 nm of iron oxide type $Fe^{2+}/Fe^{3+}$ are introduced into the mixture, so as to make the sol and the gel sensitive to the magnetic stresses that may be used to give a form during gelation or alternatively to modify the release of a compound temporarily trapped in such a gel.

After homogenization during gelation, the brown-orange colored gel is perfectly stable.

After 10 weeks, the addition of 2 ml of water does not affect its paramagnetic behavior and the supernatant solution remains colorless for a minimum of 4 months, which confirms the trapping of the PMN.

It is found that the combination in accordance with the present invention has an advantage in terms of stability.

EXAMPLE 6

Combination of PAG with Active Principles

The release of three compounds ("drug models") was tested independently:

1—cobalt acetate;

2—fluorescent poly(sodium acrylate) of molecular mass equal to 2000-2500 g/mol; and 3—the poly(tyrosine-formaldehyde) oligomer of molecular mass equal to 2600 g/mol.

Preparation Procedure:

60 mg of PAG polymer of molecular mass equal to 170 000 g/mol are placed in contact with 1 mil of physiological serum (6% by mass) in a small, hermetically sealed cylindrical flask and heated at 60° C. for a few minutes to obtain a clear, homogeneous solution, which is gelled by cooling.

The cycle is repeated twice to perfect the homogeneity of the gel.

10 mg of the compound chosen as drug model are added. The mixture is heated to have a homogeneous solution, which is left to cool to obtain the compound-gel system.

The flask is placed in a mobile incubator at 37° C. after having added on top of the gel formed 1 ml of physiological serum, into which the compound trapped in the hydrogel gradually diffuses. The receiving medium is then renewed at regular intervals and the compound that has diffused is evaluated quantitatively by UV spectrometry. The curve of gradual release is plotted as a percentage of the amount initially placed in the gel.

Figure 4:
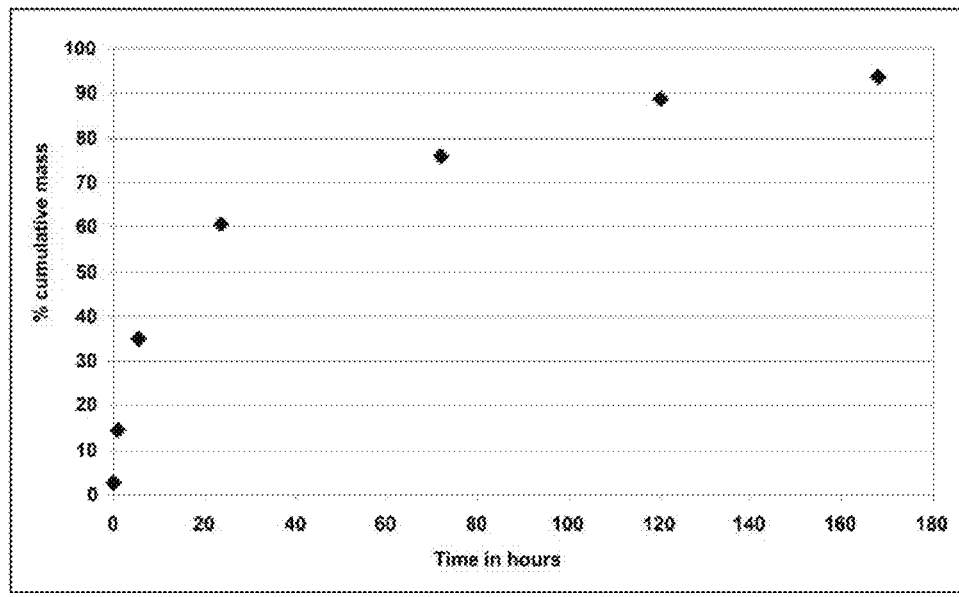

1) Example of Cobalt Acetate, Mineral Salt:

FIG. 4 shows the curve for the release of cobalt acetate in poly(N-acryloylglycinamide) with an average molar mass equal to 170 000 g/mol, as a function of time.

This curve is noteworthy by a weak "burst" (less than 15% at 1 hour) and by a gradual release until depletion is complete. The "burst" is a very short term release due to the passage into solution of the active principle available at the surface, i.e. not retained by the matrix.

In the same medium without gel, the cobalt salt without gel dissolves instantaneously in its entirety.

Figure 5:
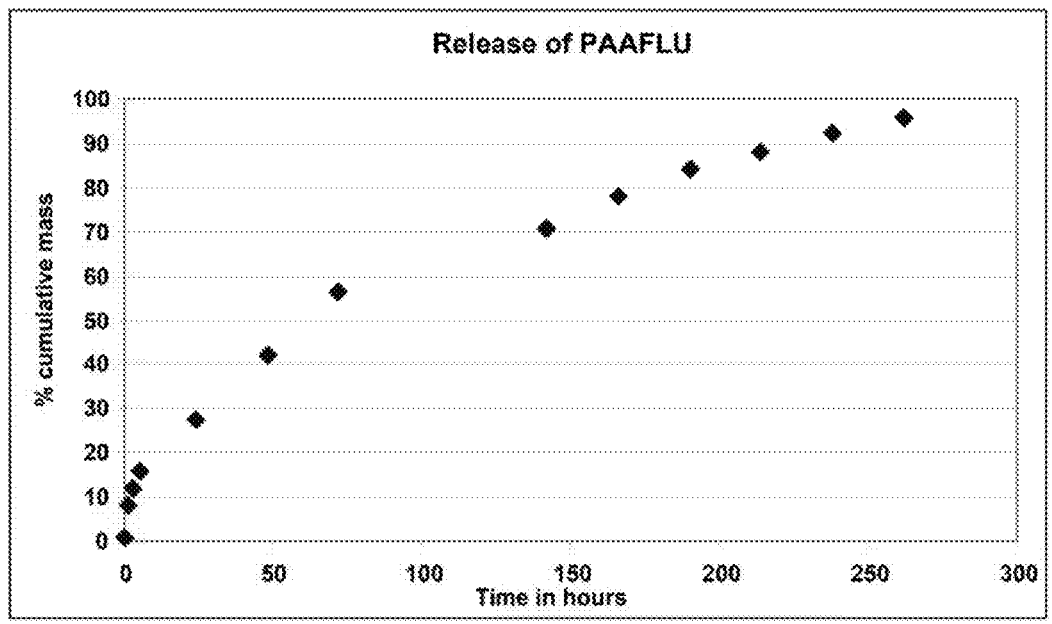

2) Example of a Poly(Sodium Acrylate) Labeled to a Level of 2% of the Repeating Units with Covalently Coupled Fluoresceinamine (PAAFLU):

FIG. 5 shows the curve of release of poly(sodium acrylate) in poly(N-acryloylglycinamide) with an average molar mass equal to 170 000 g/mol, as a function of time.

In this case also, the "burst" is very weak (less than 10%) and the gradual release continues up to depletion.

Figure 6:
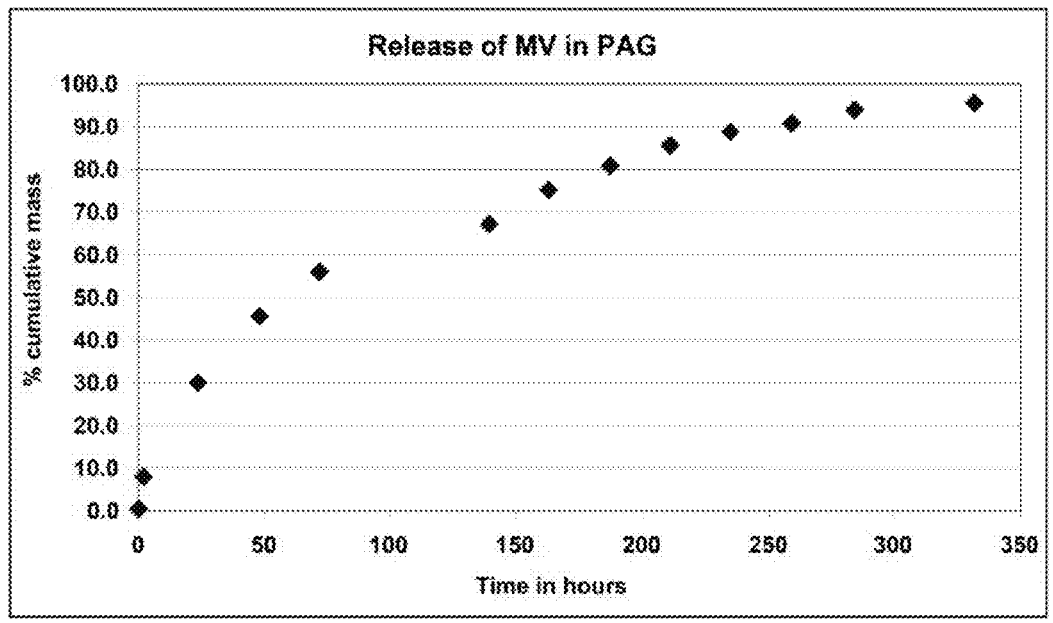

3) Example of a Poly(Tyrosine-Formaldehyde) Oligomer Referred to as MV with a Molecular Mass Equal to 2600 g/Mol:

FIG. 6 shows the curve of release of the poly(tyrosine-formaldehyde) oligomer in poly(N-acryloylglycinamide) with an average molar mass equal to 170 000 g/mol, as a function of time.

In this case also, the "burst" is weak and its release is total.

EXAMPLE 7

Injection into Mice with Methylene Blue as Antitumor Drug Model for Intraperitoneal Administration The delivery of the dye from the charged hydrogel to the tissues and organs of the intraperitoneal cavity in mice is observed.

To do this, an isotonic solution of PAG (molar mass equal to about 176 000 g/mol, 6% by weight of PAG) containing methylene blue (4 ml of solution (20 mg of dye) per 16 ml of gel) formed at 60° C. conditioned is introduced into heated syringes to be injected rapidly at 45° C. through a 23-gauge needle in order to fill the intraperitoneal cavity of the mice.

The mice treated according to the regulatory procedures were sacrificed after 2 hours, 8 hours, 24 hours, 30 hours and 52 hours (two animals per point).

After opening the abdomen, the distributions of the blue color in the gel, the tissues and the organs were assessed visually and compared at the same times with those observed for the control mice which received by similar injection an isotonic solution of the same concentration of methylene blue.

On the treated mice, the delayed presence of the dye was observed in the fat of the intestinal and abdominal tissues with a persistent coloration in the peritoneum and the abdominal organs that was still detectable after 52 hours, the gel decolorizing gradually. Specifically, the gel, tissues and organs, especially the liver, remained colored for at least 52 hours.

On the control mice, the blue color totally disappeared after 24 h.

These results show that an injected PAG gel does indeed give rise to a delay effect in vivo and that it may be exploited for the gradual release of a model molecule temporarily trapped in the intraperitoneal cavity.

The invention claimed is:

1. A combination of poly(N-acryloylglycinamide) with at least one active principle and/or at least one product that is visible in medical imaging, in a physiologically acceptable aqueous medium, wherein said active principle is chosen from antitumor agents, antibiotics, analgesics, anti-inflammatory agents, growth factors and antiseptics, wherein said product that is visible in medical imaging is chosen from an opacifier, a fluorescer and an ionizing radiation emitter wherein the combination has a gel-sol transition temperature of between 30 and 60° C., and being in liquid form above the gel-sol transition temperature and in gel form below the gel-sol transition temperature, and the combination being useful (i) for local post-operative or preoperative treatment, (ii) for treating wounds, wherein it is applied directly to the wound or via any protective device, or (iii) for post-operative monitoring by medical imaging.

2. The combination as claimed in claim 1, wherein said poly(N-acryloylglycinamide) has an average molar mass of between 10 000 and 1 000 000 g/mol.

3. The combination as claimed in claim 1, wherein said poly(N-acryloylglycinamide) is present in the aqueous medium in a solids content of between 0.5% and 20% by weight, relative to the total weight of said medium.

4. The combination as claimed in claim 1, wherein said aqueous medium is prepared based on a physiological liquid.

5. The combination as claimed in claim 1, wherein said active principle is an antitumor agent.

6. The combination as claimed in claim 1, which is useful for delivering an active principle.

7. The combination as claimed in claim 1, which is useful for patients who have undergone a tumor reduction surgery.

8. The combination as claimed in claim 1, wherein it is applied to a wound via an impregnated protective device.

9. The combination as claimed in claim 1, which is useful for treating animals, and humans.

10. A lyophilizate of claim 1 prepared from an aqueous solution of poly(N-acryloylglycinamide), and of at least one active principle and/or at least one product that is visible in medical imaging, wherein the combination of polv(N-acryloylglycinamide) with at least one active principle and/or of at least one product that is visible in medical imaging has a gel-sol transition temperature of between 30 and 60°

C., and being in liquid form above the gel-sol transition temperature and in gel form below the gel-sol transition temperature wherein said active principle is chosen from antitumor agents, antibiotics, analgesics, anti-inflammatory agents, growth factors and antiseptics, wherein said product that is visible in medical imaging is chosen from an opacifier, a fluorescer and an ionizing radiation emitter.

* * * * *